(12) United States Patent
Purcell et al.

(10) Patent No.: US 6,607,543 B2
(45) Date of Patent: Aug. 19, 2003

(54) LANCING MECHANISM

(75) Inventors: D. Glenn Purcell, Edwardsburg, MI (US); Allen J. Brenneman, Goshen, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/861,438

(22) Filed: May 21, 2001

(65) Prior Publication Data

US 2001/0056284 A1 Dec. 27, 2001

Related U.S. Application Data

(60) Provisional application No. 60/211,269, filed on Jun. 13, 2000.

(51) Int. Cl.$^7$ .............................................. A61B 17/14
(52) U.S. Cl. ...................................................... 606/181
(58) Field of Search ............................ 606/1, 181–185; 600/573, 583

(56) References Cited

U.S. PATENT DOCUMENTS

| | | | | |
|---|---|---|---|---|
| 3,797,488 A | * | 3/1974 | Hurschman et al. | 604/136 |
| 4,449,529 A | * | 5/1984 | Burns et al. | 606/182 |
| 4,517,978 A | * | 5/1985 | Levin et al. | 606/182 |
| 4,735,203 A | * | 4/1988 | Ryder et al. | 606/182 |
| 5,196,025 A | * | 3/1993 | Ranalletta et al. | 600/583 |
| 5,267,963 A | * | 12/1993 | Bachynsky | 604/134 |
| 5,304,193 A | * | 4/1994 | Zhadanov | 600/585 |
| 5,318,583 A | * | 6/1994 | Rabenau et al. | 606/182 |
| 5,527,334 A | * | 6/1996 | Kanner et al. | 600/583 |
| 5,628,764 A | * | 5/1997 | Schraga | 606/181 |
| 5,741,288 A | * | 4/1998 | Rife | 606/181 |
| 6,022,366 A | * | 2/2000 | Schraga | 606/181 |
| 6,231,531 B1 | * | 5/2001 | Lum et al. | 600/573 |

* cited by examiner

*Primary Examiner*—Kevin T. Truong
*Assistant Examiner*—Victor Nguyen
(74) *Attorney, Agent, or Firm*—Jerome L. Jeffers

(57) ABSTRACT

A lancing mechanism for puncturing skin is provided. The lancing mechanism comprises a lance having a penetration end which is adapted to puncture skin. The penetration end of the lance is movable from a first position to a second position during a forward stroke and between the second position and the first position during a return stroke. A forcing plunger applies a force to the lance to move the lance from the first position to the second during the forward stroke. The forcing plunger is adapted to engage the lance during the forward stroke to move the penetration end of the lance from the first position to the second position and to disengage the lance when the penetration end of the lance approaches the second position. A first resilient member coupled to the lance moves the first end of the lance from the second position to the first position during the return stroke.

23 Claims, 8 Drawing Sheets

LANCING MECHANISM

This application claims the benefit of Provisional Application No. 60/211,269 filed Jun. 13, 2000.

FIELD OF THE INVENTION

The present invention relates generally to blood monitoring devices, and, more particularly, to a lancing mechanism for lancing a user's skin to obtain a sample of blood for analysis.

BACKGROUND OF THE INVENTION

It is often necessary to quickly obtain a sample of blood and perform an analysis of the blood sample. Preferably, the obtaining of blood is as painless as possible. One example of a need for painlessly obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are both potentially life-threatening emergencies.

One method of monitoring a person's blood glucose level is with a portable, hand-held blood glucose testing device. The portable nature of these devices enables the users to conveniently test their blood glucose levels wherever the user may be. In order to check the blood glucose level, a drop of blood is obtained from the fingertip using a separate lancing device. The lancing device contains a needle lance to puncture the skin. Once the requisite amount of blood is produced on the fingertip, the blood is harvested using the blood glucose testing device. The blood is drawn inside of the testing device which then determines the concentration of glucose in the blood. The results of the test are communicated to the user via a display on the testing device.

Many prior art lancing devices implement a spring coupled to the actual lance to move the lance to its penetration depth. The lance is drawn back to compress the spring. When released, the spring extends thus forwardly propelling the lance to its penetration depth. One problem associated with some prior art lancing devices is that the penetration depth of those lances is dependant on a spring constant which is a measure of the spring's stiffness. The mechanical qualities of a spring, including the stiffness, tend to degrade over time with use. Accordingly, over time, the penetration depth of many prior art lances may vary. When the penetration depth of the lance lessens over time, the lance may not produce a laceration deep enough to draw the requisite volume of blood necessary for blood glucose analysis. An insufficient lancing can result in an erroneous analysis if the user does not recognize that the lancing has not produced the requisite volume of blood for analysis. Or, if the user does recognize an insufficient lancing has occurred, the user must re-lance resulting in another laceration in the user's skin and more pain. The user may eventually have to replace the lance which has degraded over time.

Another related problem associated with many of the aforementioned prior art lancing devices is that when the spring forwardly advances the lance to its penetration depth, the spring extends past its static length. The spring then retracts the lance; however, due to the oscillatory nature of the spring, the lance is retracted past its static length. The lance continues to oscillate in this manner thus entering the laceration created in the user's skin several times. Put another way, with each actuation of a prior art lancing device, a user's skin is lanced several times which results in a larger laceration. A larger laceration in the user's skin translates into more pain for the user and a longer time for the laceration to heal.

Accordingly, there exists a need for a lancing mechanism which moves a lance a known stroke not dependent on a spring constant and the extension of the spring past its static length.

SUMMARY OF THE INVENTION

A lancing mechanism for puncturing skin is provided. The lancing mechanism comprises a lance having a penetration end which is adapted to puncture skin. The penetration end of the lance is movable from a first position to a second position during a forward stroke and between the second position and the first position during a return stroke. A forcing plunger applies a force to the lance to move the lance from the first position to the second during the forward stroke. The forcing plunger is adapted to engage the lance during the forward stroke to move the penetration end of the lance from the first position to the second position and to disengage the lance when the penetration end of the lance approaches the second position. A first resilient member coupled to the lance moves the first end of the lance from the second position to the first position during the return stroke.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

Other objects and advantages of the invention will become apparent upon reading the following detailed description in conjunction with the drawings in which.

DETAILED DESCRIPTION OF THE PREFERRED EMBODIMENTS

Figure 1A:
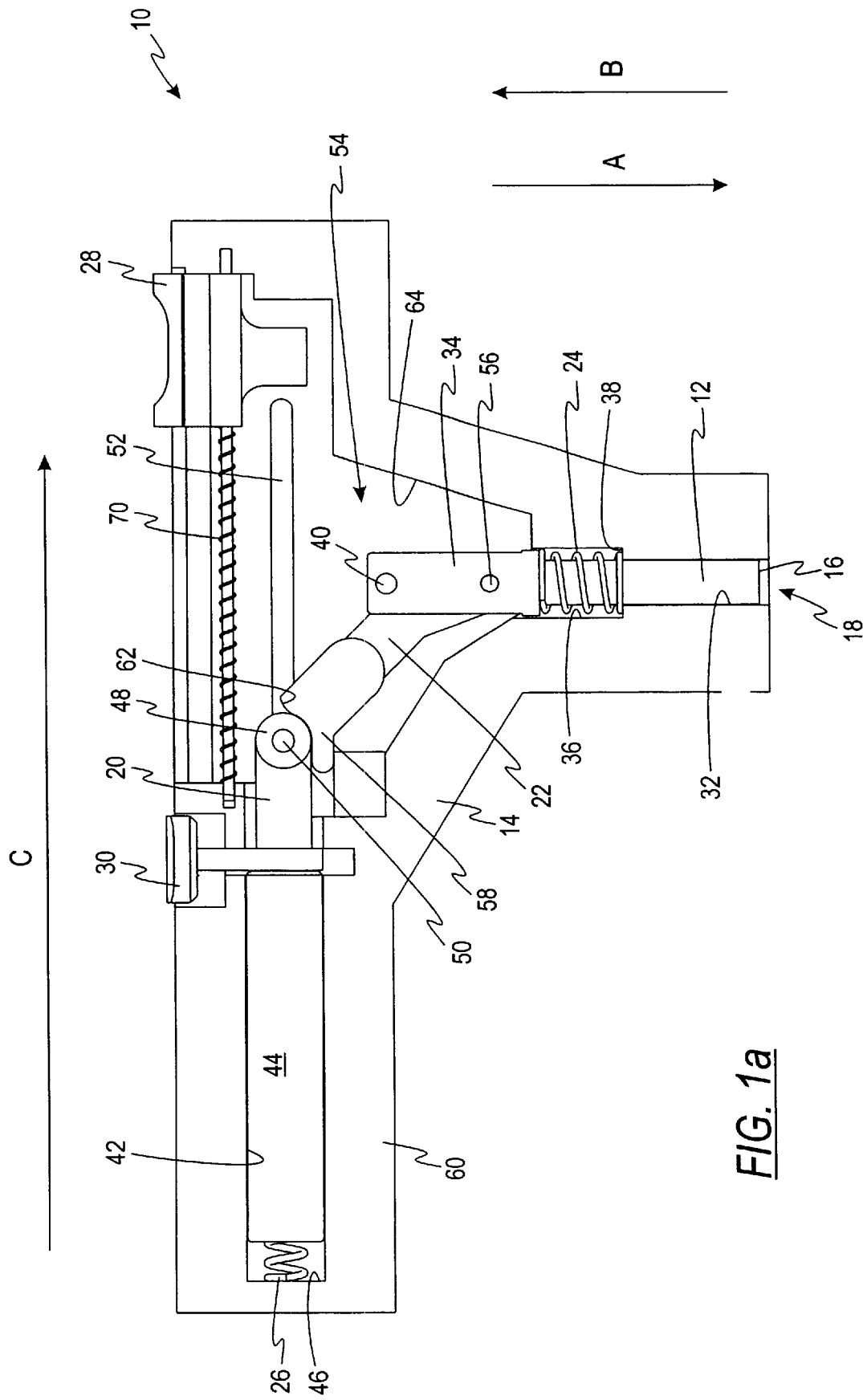
FIG. 1a is a side view of a lancing mechanism shown in a pre-firing position according to one embodiment of the present invention.
Figure 1B:
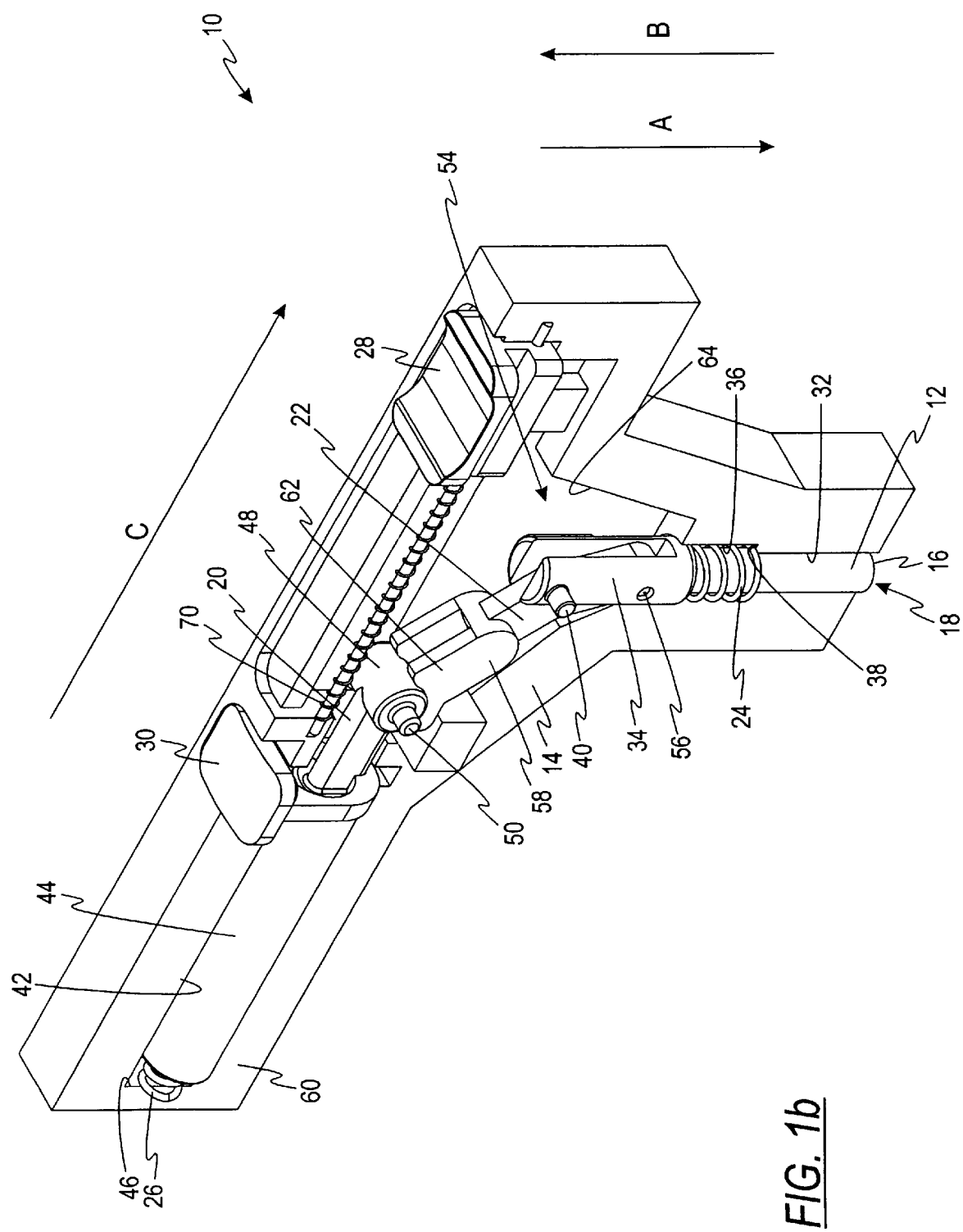
FIG. 1b is a perspective view of a lancing mechanism shown in a pre-firing position according to one embodiment of the present invention.

Referring now to FIGS. 1a and 1b, a lancing mechanism 10 of the present invention will be described in greater detail. The lancing mechanism 10 includes a lance 12 disposed within a housing 14. The lance 12 has a sharp penetration end 16 which is capable of puncturing skin to obtain of drop of blood for analysis. To obtain a sample of blood, the penetration end 16 of the lance 12 extends beyond the housing 14 through an aperture 18 disposed in the housing 14 to puncture a user's skin. After making the initial laceration in the user's skin, the lance 12 is drawn back within the housing 14.

The lancing mechanism 10 is designed to fire the lance 12 without experiencing the aforementioned oscillations associated with prior art lancing devices. During a forward stroke, the penetration end 16 of the lance 12 is moved to its penetration depth while engaged by a forcing plunger 20 via a linkage 22. Once the penetration end 16 of the lance has reached its penetration depth, the lance 12 begins its return stroke wherein a first compression spring 24 causes the lance 12 to ascend back into the bounds of the housing 14.

The forcing plunger 20 provides the force necessary to move the penetration end 16 of the lance 12 through a user's skin to the penetration depth. The forcing plunger 20 transmits the force provided to it by a second compression spring 26 through the linkage 22 to the lance 12. In order to produce the requisite force, the forcing plunger 20 is drawn back to the pre-firing position with a slider 28 thus compressing the second compression spring 26. In the pre-firing position, the forcing plunger 20 is held in place by a trigger 30. When depressed, the trigger 30 releases the forcing plunger 20 thus firing the lancing mechanism 10.

The lancing device 10 of the present invention remedies the aforementioned problems associated with prior art lancing devices by moving the lance 12 a known length during a forward stoke with a linkage 22. The penetration depth of the lance is not based on a spring constant and the extension of that spring past the static length of the spring.

The lance 12 which is positioned in the housing in a pre-firing position (FIG. 1a) is movable in the direction indicated by arrow A during the forward stroke and in the direction indicated by arrow B during the return stroke. The housing 14 contains a first channel 32 which constrains the lateral movement of the lance 12. The first channel 32 is substantially parallel to a longitudinal axis of the lance 12. The lance 12 has a base 34 which travels along with the lance 12 in a second channel 36. The first compression spring 24 is disposed in the second channel 36 between the base 34 and a shelf 38 formed at the intersection of the second channel 36 and the first channel 32. The base 34 contains an outwardly extending tab 40 which mates with a corresponding linear slot 41 (FIG. 3a) disposed within the housing 14. The tab 40 and the corresponding linear slot 41 maintain the linear alignment of the base 34.

Figure 3A:
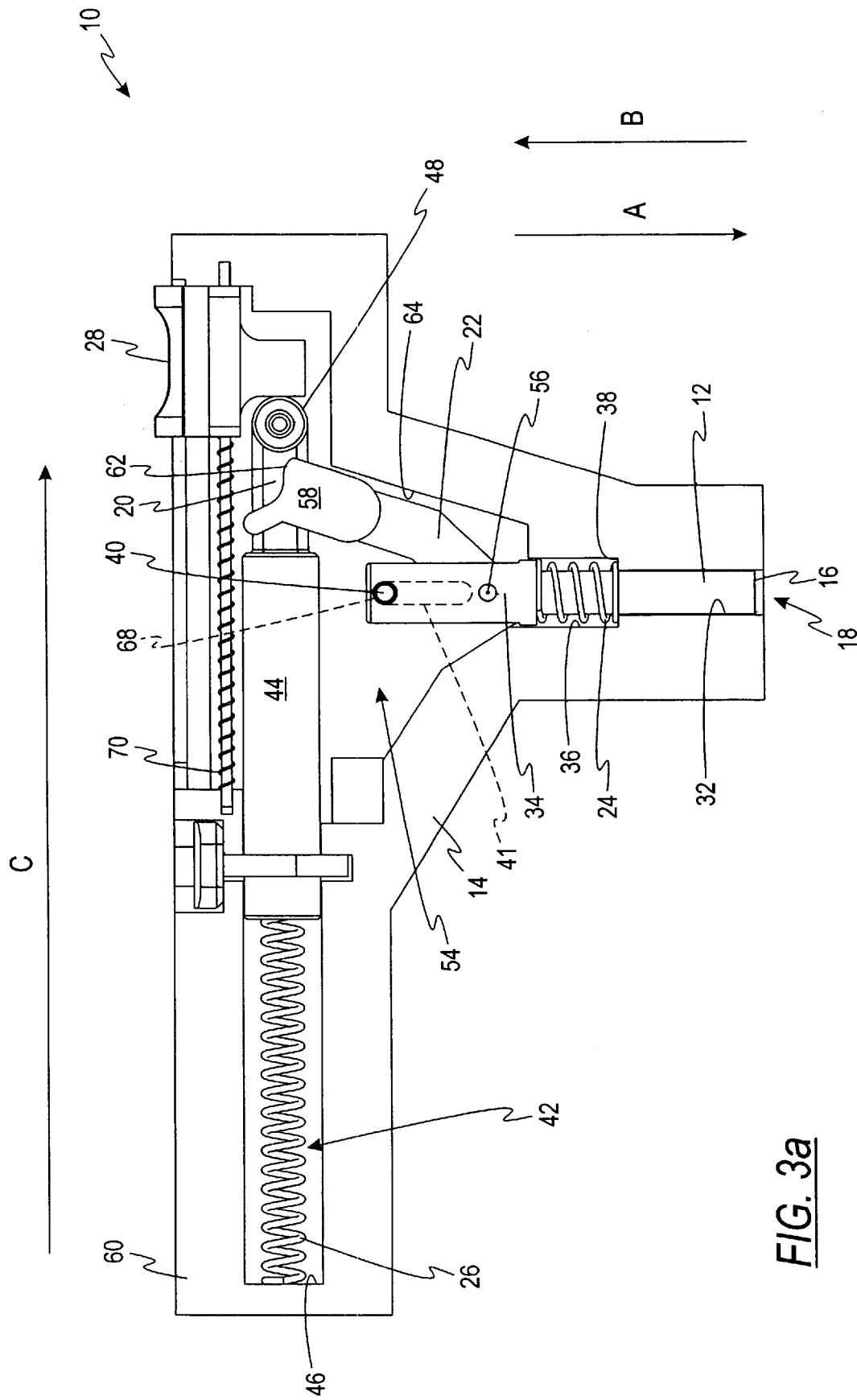
FIG. 3a is side view of a lancing mechanism shown in a post-firing position according to one embodiment of the present invention.

The housing 14 contains a third channel 42 which constrains the lateral movement of the forcing plunger 20. The third channel 42 is substantially parallel to a longitudinal axis of the forcing plunger 20. The forcing plunger 20 is disposed within the housing 14 substantially perpendicular to the lance 12. The second compression spring 26 is disposed between a base 44 of the forcing plunger 20 and the a base 46 of the third channel 42. The forcing plunger 20 moves in the direction indicated by the arrow C from a pre-firing position (FIG. 1a) to a post-firing position (FIG. 3a). The movement of the forcing plunger 20 from the pre-firing position to the post-firing position coincides with the forward and return stroke of the lance 12. The forcing plunger 20 has a rounded end 48 which contains outwardly extending tabs 50 which mate with corresponding slots 52 disposed in the housing 14. The combination of the outwardly extending tabs 50 and the corresponding slots 52 aide in maintaining the linear movement of the forcing plunger 20 when advancing from the pre-firing position to the post-firing position.

The housing 14 contains a hollow portion 54 to accommodate the rotation of the linkage 22 during the operation of the lancing mechanism. The linkage 22 is pivotally coupled to the base 34 via a pin 56. The linkage has a curved receiving end 58 which is designed to engage the rounded end 48 of the forcing plunger 20. When the forcing member moves in the direction indicated by the arrow C, the forcing member 20 contacts the linkage 22 thus forcing the lance 12 downward in the direction indicated by arrow A.

The operation of the lancing mechanism 12 will now be described starting with FIGS. 1a and 1b. In order to lance a user's skin, a user holds the lancing mechanism 10 by a handle portion 60 of the housing 14 in a manner such that the portion of the housing 14 containing the aperture 18 is pressed against the user's skin. In FIGS. 1a and 1b, the forcing plunger 20 is shown in the pre-firing position. The user depresses the trigger 30 of the lancing mechanism 10 to release the forcing plunger 20. Upon being released, the forcing plunger 20 rapidly accelerates in the direction indicated of the arrow C. In the pre-firing position, the rounded end 48 of the forcing plunger 20 is substantially in contact with the curved receiving end 58 of the linkage 22. The curved receiving end 58 contains a lip 62 which maintains the contact between the curved receiving end 58 of the linkage 22 and the rounded end 48 of the forcing plunger 20. The linear movement of the plunger 20 in the direction of the arrow C forces the linkage 22 to move linearly in the direction of arrow A and to rotate in the clockwise direction. In turn, the aforementioned movement of the linkage 22 forces the lance 12 linearly downward in the direction of the arrow A.

To summarize, depression of the trigger 30 fires the forcing plunger 20. The forcing plunger 20 rapidly advances from the pre-firing position in the direction of arrow C. The forcing plunger 20 engages the linkage 22 which in turn propels the lance 12 downward in the direction of arrow A.

Figure 2A:
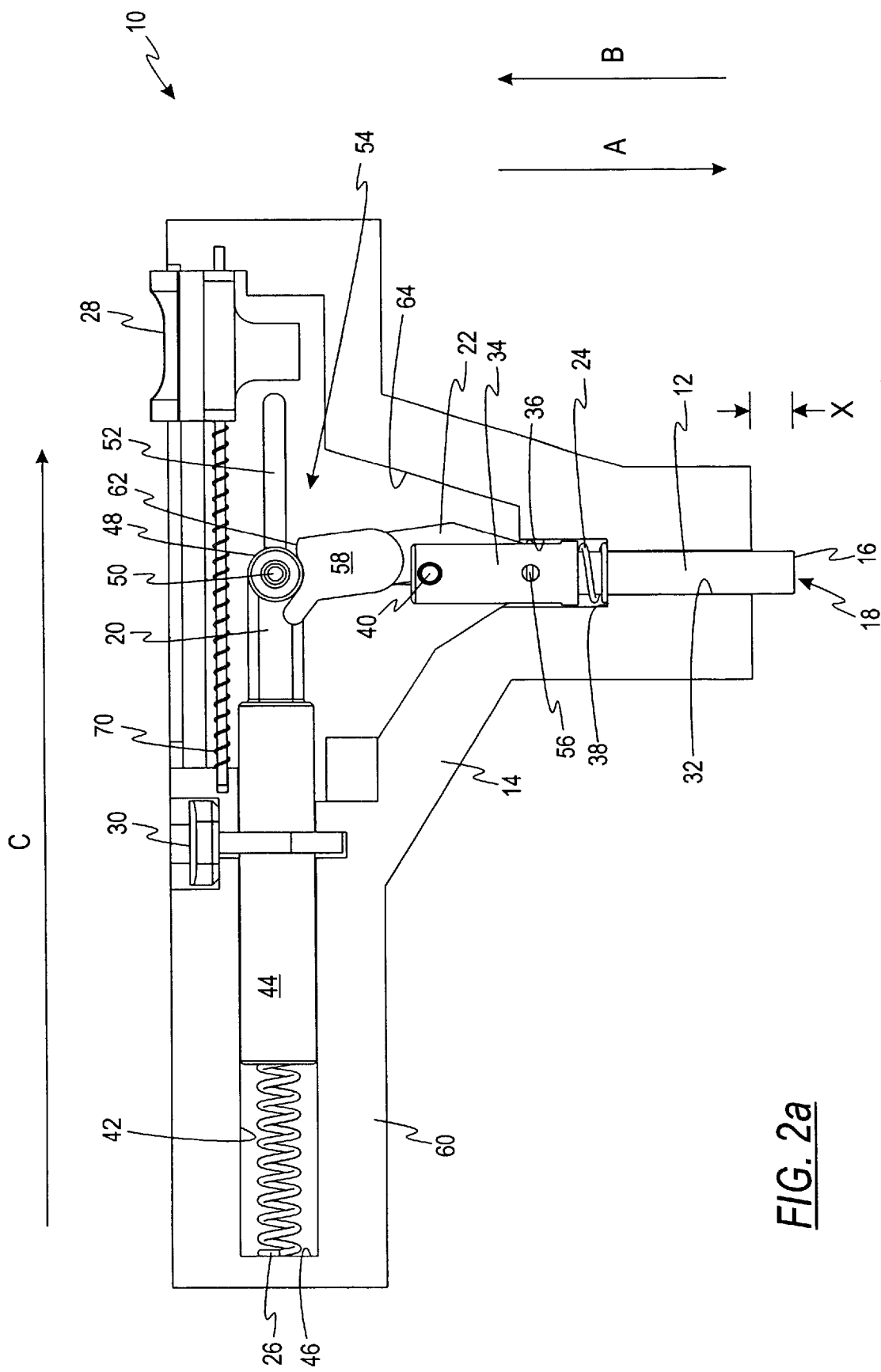
FIG. 2a is a side view of a lancing mechanism shown at the approximate conclusion of a forward stoke of a lance according to one embodiment of the present invention.
Figure 2B:
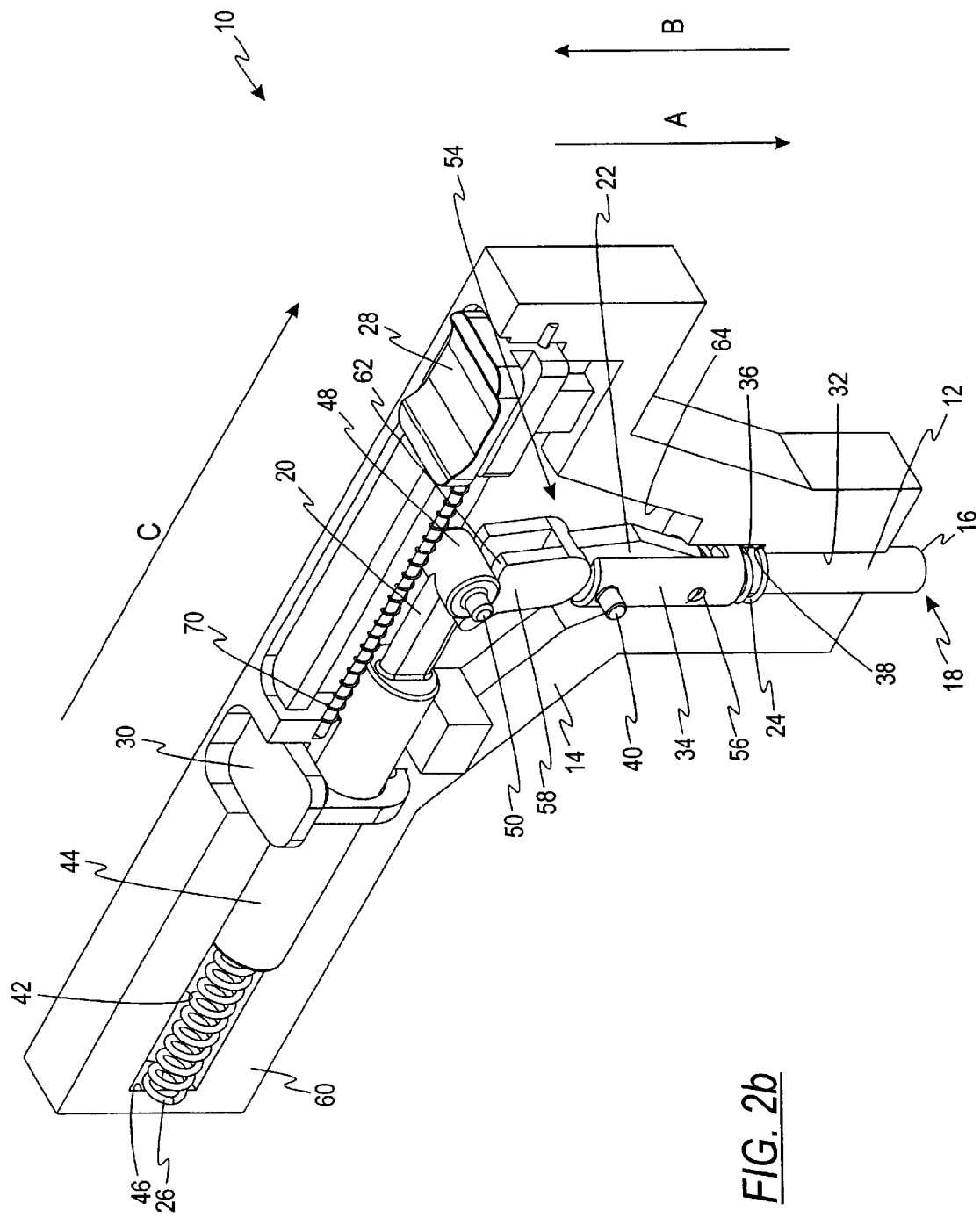
FIG. 2b is a perspective view of a lancing mechanism shown at the approximate conclusion of a forward stoke of a lance according to one embodiment of the present invention.

Turning now to FIGS. 2a and 2b, the linkage 22 has rotated in the clockwise position such that it is shown in approximately the twelve o'clock position. When in the twelve o'clock position, the linkage 22 has also been moved downward by the forcing plunger 20 a distance sufficient for the lance 12 to extend beyond the housing a distance X about equivalent to the penetration depth. The forward stroke of the lance 12 concludes when the distance X is at a maximum. The forcing plunger 20 continues to move in the direction of the arrow C which in turn further rotates the linkage 22 in the clockwise direction.

Figure 3B:
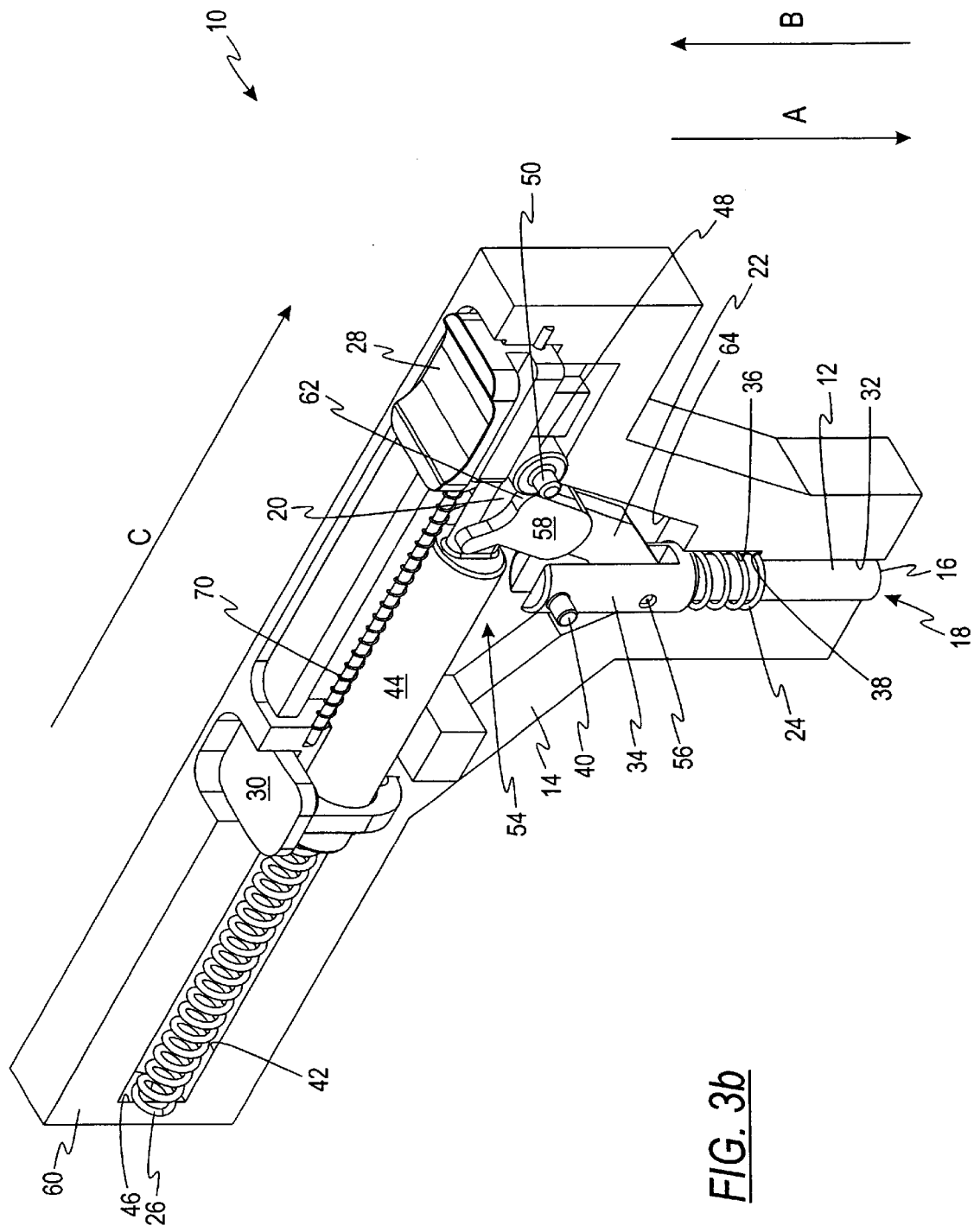
FIG. 3b is perspective view of a lancing mechanism shown in a post-firing position according to one embodiment of the present invention.

Turning now to FIGS. 3a and 3b, as the forcing plunger 20 continues to travel in the direction indicated by the arrow C, the curved receiving end 58 of linkage 22 continues to engage the forcing plunger 20 during which the linkage 22 continues its clockwise rotation. However, once the forward stroke is complete, the linkage 22 is no longer being forced downward by the receiving member 20. The continued movement by the forcing member 20 in the direction of arrow C creates room for the first compression spring 24 to advance the lance 12 and in turn the linkage 22 upward in the direction of the arrow B. The linkage 22 continues to rotate in the clockwise direction, until the linkage 22 contacts a wall 64 which prohibits any further clockwise rotation of the linkage 22. When the linkage 22 contacts the wall 64, the lip 62 of the curved receiving end 58 is substantially in the horizontal position allowing the forcing plunger to push past the lip 62 and continue to travel in the direction of the arrow C until contacting a slider 28

After the linkage 22 has disengaged the forcing member 20, the first compression spring 24 forces the lance 12 and the linkage 22 upward to the position shown in FIGS. 3a and 3b. No.oscillation of the lance 12 occurs because the first compression spring 24 is prohibited from extending to its static length. The outwardly extending tab 40 on the base 34 of the lance 12 engages an upper end 68 of the slot 41 to prevent any further movement of the lance in the direction of the arrow B.

To summarize, a firing of the lancing mechanism 10 results in only one forward and one return stroke of the lance 12. The lancing mechanism 10 eliminates the multiple oscillations of the lance into and out of the laceration created in the user's skin which is a problem associated with some prior art lancing devices. This problem is remedied because the length of the forward stroke of the lance 12 of the lancing mechanism 10 is not dependant on the spring constant of a spring which moves a prior art lance and the extension of that spring past its static length. In the present invention, the forward stroke of the lance 12 is dependant on the length of the linkage 22. Accordingly, in various embodiments of the present invention, the length of the linkage 22 is varied in order to change the penetration depth of the lancing device 12. The penetration depth of the lancing mechanism 10 remains consistent over the life of the lancing mechanism 10 because the penetration depth is dependant on the length of the linkage 22. Conversely, the penetration depth of a prior art lance tends to degrade over time because the mechanical properties of the spring which moves the lance tend to degrade over time. Any oscillations of the lance 12 due to the first compression spring 24 are suppressed and do not cause repeated lancings because the combination of the tab 40 and the slot 41 prohibit the spring 24 from extending past its static length.

Figure 4A:
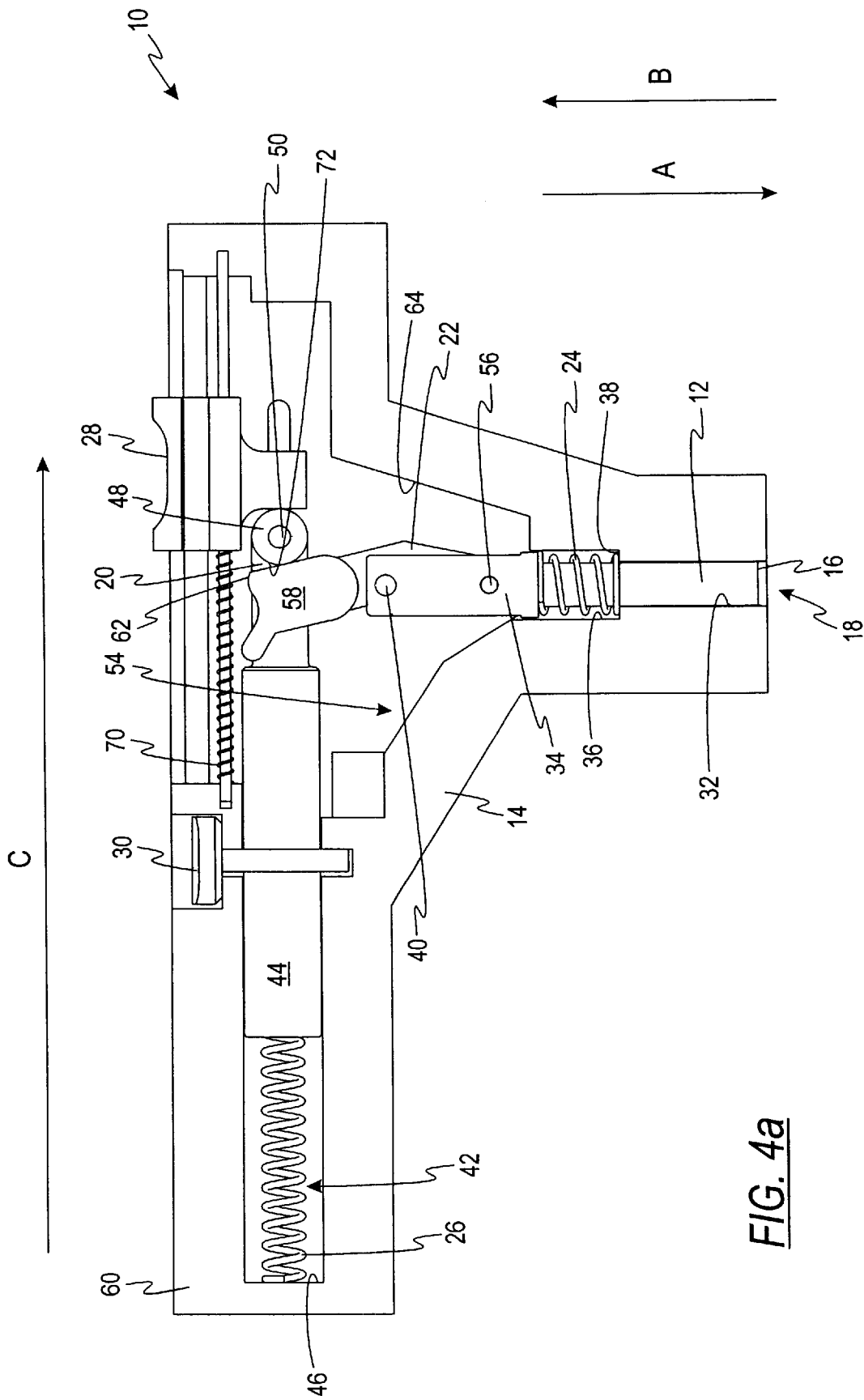
FIG. 4a is a side view of a lancing mechanism shown in a mid-return position according to one embodiment of the present invention.
Figure 4B:
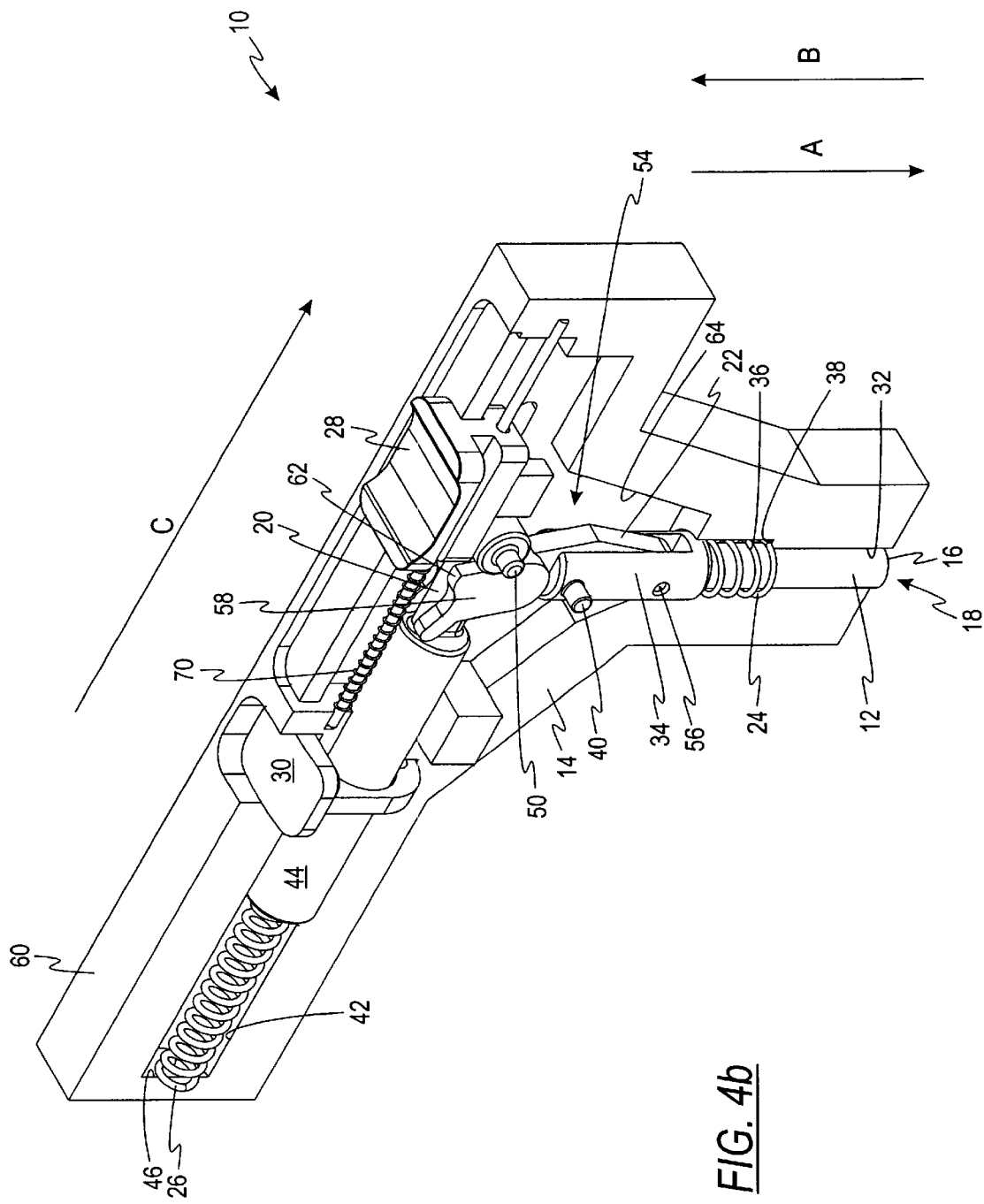
FIG. 4b is a perspective view of a lancing mechanism shown in a mid-return position according to one embodiment of the present invention.

Turing now to FIGS. 4a and 4b, the lancing mechanism 10 is shown with the slider 28 drawing the forcing plunger 20 from the post-firing position (FIG. 3a) to the pre-firing position (FIG. 1a). The slider 28, which is biased in the far right position by a third compression spring 70 as shown in FIG. 3a, is used to move the lancing mechanism 10 back into the pre-firing position. After the lance has been fired, the user simply slides the slider 28 to the left as viewed in FIG. 4a to ready the lancing mechanism 10 for firing. The sliding of the forcing plunger 20 pushes the linkage 22 into place for firing. As the plunger 20 slides to the left as viewed in FIG. 4a, a backside 72 of the forcing plunger 20 contacts the linkage 22 causing the linkage 22 to rotate in the counter-clockwise direction to the firing position. Once the forcing plunger 20 pushes past the linkage 22, a wire spring (not shown) biases the linkage 22 back in the clockwise direction so that the curved receiving end 58 of the linkage 22 engages the rounded end 48 of the plunger. The third spring 70 biases the slider 28 back to the right so that the slider 28 does not interfere with the forcing plunger 20 during the firing of the lancing mechanism 10.

The lancing mechanism 10 is designed to be light-weight and compact allowing the user to carry the lancing mechanism 10 on the user's person. In order to reduce the weight of the lancing mechanism 10, the various structural components such as the housing 14, the forcing plunger 20, the linkage 22, the slider 28, the trigger 30, etc. are made out of a light-weight, rigid material such as, for example, plastic. The lancing mechanism 10 is also designed so that the user can operate the mechanism 10 with a single hand thus freeing the fingers of the user's other hand for lancing. In operation, the user grasps the handle 60 portion of the housing 14 with the user's left-hand, for example. The user contacts the portion of the housing 14 containing the aperture 18 against the user's skin, such as the skin on one of the user's right-hand fingers. The user then depresses the trigger 30 with a left-hand finger or thumb to fire the lancing mechanism.

While the invention is susceptible to various modifications and alternative forms, specific embodiments thereof have been shown by way of example in the drawings and will be described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A lancing mechanism for puncturing skin, comprising:
   a lance having a penetration end being adapted to puncture skin, the penetration end of the lance being movable from a first position to a second position during a forward stroke, the penetration end of the lance being movable between the second position and the first position during a return stroke;
   a forcing plunger being adapted to apply a force to the lance to move the lance from the first position to the second during the forward stroke, the forcing plunger being adapted to engage the lance during the forward stroke to move the penetration end of the lance from the first position to the second position, the forcing plunger being adapted to disengage the lance when the penetration end of the lance is in the second position; and
   a first resilient member coupled to the lance being adapted to move the first end of the lance from the second position to the first position during the return stroke.

2. The lancing mechanism of claim 1 further comprising a housing wherein the forcing plunger, the lance, and the first resilient member are disposed within the housing, the housing having an aperture disposed therein, the penetration end of the lance being bounded by the housing when in the first position, the penetration end of the lance extending through the aperture when in the second position.

3. The lancing mechanism of claim 2 farther comprising a linkage having a first end and a second end disposed within the housing between the forcing plunger and the lance, the linkage being adapted to couple the forcing plunger to the lance during the forward stroke, the second end of the linkage being pivotally coupled to the lance, the first end of the linkage being adapted to engage the forcing plunger during the forward stroke and to disengage the forcing plunger during the return stoke.

4. The lancing mechanism of claim 3 wherein the forcing plunger has a rounded end and the first end of the linkage is generally C-shaped.

5. The lancing mechanism of claim 4 wherein the generally C-shaped first end of the linkage has a lip, the lip being adapted to engage the rounded end of the forcing plunger.

6. The lancing mechanism of claim 5 wherein the forcing plunger is movable from a pre-firing position to a post-firing position when applying the force to the lance, the mechanism further comprising a second resilient member being adapted to move the forcing plunger from the pre-firing position to the post-firing position.

7. The lancing mechanism of claim 6 wherein the lip is adapted to disengage the rounded end of the forcing plunger as the forcing plunger nears the post-firing position.

8. The lancing mechanism of claim 6 wherein the second resilient member is a compression spring.

9. The lancing mechanism of claim 6 further comprising a trigger being adapted to release the forcing plunger from the pre-firing position.

10. The lancing mechanism of claim 1 in combination with a blood glucose testing device.

11. The lancing mechanism of claim 1 wherein the first resilient member is a compression spring.

12. A lancing mechanism for puncturing skin in order to obtain a sample of blood, the mechanism comprising:
a housing;
a lance disposed within the housing, the lance having a penetration end being adapted to puncture skin, the lance being moveable in a direction substantially parallel to a longitudinal axis of the lance, the penetration end of the lance being movable from a first position to a second position during a forward stroke, the penetration end of the lance being movable between the second position and the first position during a return stroke;
a forcing plunger disposed within the housing such that a longitudinal axis of the forcing plunger is substantially perpendicular to the longitudinal axis of the lance, the forcing plunger being movable in a direction substantially parallel to the longitudinal axis of the forcing plunger from a pre-firing position to a post-firing position, the forcing plunger having a first end and a second end,
a first resilient member being adapted to move the forcing plunger from the pre-firing position to the post-firing position;
a linkage member having a first end and a second end, the second end of the lance being pivotally coupled to the lance, the first end of the linkage member being adapted to engage the forcing plunger during the forward stroke to move the penetration end from the first position to the second position, the first end of the linkage member moving in a direction substantially parallel to the longitudinal axis of the forcing plunger during the forward stoke, the second end of the linkage member moving in a direction substantially parallel to the longitudinal axis of the lance during the forward stroke, the first end of the linkage member being adapted to disengage the forcing plunger during the return stoke; and a second resilient member being adapted to move the penetration end from the second position to the first position during the return stroke.

13. The lancing mechanism of claim 12 wherein the first resilient member is a compression spring.

14. The lancing mechanism of claim 12 wherein the second resilient member is a compression spring.

15. The lancing mechanism of claim 12 in combination with a blood glucose testing device.

16. The lancing mechanism of claim 12 further comprising a trigger being adapted to release the forcing plunger from the pre-firing position.

17. The lancing mechanism of claim 12 wherein the first end of the forcing plunger is generally rounded and the first end of the linkage is generally C-shaped.

18. The lancing mechanism of claim 17 wherein the generally C-shaped first end of the linkage has a lip, the lip being adapted to engage the generally rounded first end of the forcing plunger.

19. The lancing mechanism of claim 18 wherein the lip is adapted to disengage the rounded end of the forcing plunger as the forcing plunger nears the post-firing position.

20. A method for lancing a user's skin to obtain a sample of blood with a lancing mechanism, the lancing mechanism including a forcing plunger, a linkage having a first and a second end, and a lance, the first end of the linkage being pivotally coupled to the lance, the method comprising:
propelling the forcing plunger from a pre-firing position to a post-firing position with a first resilient member;
engaging the linkage pivotally coupled to a lance with the forcing plunger;
moving the lance from a first position to a second position with the forcing plunger engaged to the linkage during a forward stroke of the lance; and
disengaging the forcing plunger from the linkage.

21. The method of claim 20 further comprising moving the lance from the second position to the first position with a second resilient member.

22. The method of claim 21 further comprising moving the forcing plunger from the post-firing position to the pre-firing position with a slider.

23. The method of claim 22 further comprising maintaining the forcing plunger in the pre-firing position with a trigger.

* * * * *